(12) United States Patent
Hillebrand

(10) Patent No.: US 8,551,149 B2
(45) Date of Patent: Oct. 8, 2013

(54) CORRECTIVE METHOD FOR FINGERNAILS OR TOENAILS

(76) Inventor: Christa Hillebrand, Rottach-Weissach (DE)

(*) Notice: Subject to any disclaimer, the term of this patent is extended or adjusted under 35 U.S.C. 154(b) by 17 days.

(21) Appl. No.: 13/498,897

(22) PCT Filed: Sep. 29, 2010

(86) PCT No.: PCT/EP2010/064439
§ 371 (c)(1),
(2), (4) Date: Mar. 28, 2012

(87) PCT Pub. No.: WO2011/039243
PCT Pub. Date: Apr. 7, 2011

(65) Prior Publication Data
US 2012/0191033 A1    Jul. 26, 2012

(30) Foreign Application Priority Data
Sep. 29, 2009 (DE) .................. 10 2009 043 355

(51) Int. Cl.
*A61F 5/11* (2006.01)
*A61N 5/06* (2006.01)

(52) U.S. Cl.
USPC ............................... 607/88; 602/31; 128/898

(58) Field of Classification Search
USPC ............... 607/88, 89, 96; 602/31; 128/898
See application file for complete search history.

(56) References Cited

U.S. PATENT DOCUMENTS

| | | | |
|---|---|---|---|
| 3,981,298 A | 9/1976 | Vironda | |
| 5,261,872 A | 11/1993 | Goldenberg | |
| 5,370,140 A * | 12/1994 | Meyerovich | 132/200 |
| 6,095,995 A * | 8/2000 | Machida | 602/30 |
| 2004/0156801 A1 | 8/2004 | Okada | |
| 2008/0287912 A1 | 11/2008 | Horrigan | |

FOREIGN PATENT DOCUMENTS

| | | |
|---|---|---|
| DE | 44 46 650 C2 | 6/1996 |
| DE | 696 17 484 T2 | 8/1996 |
| WO | WO 2009/065533 | 3/2009 |

* cited by examiner

*Primary Examiner* — Sam Yao
*Assistant Examiner* — Michael M Kim
(74) *Attorney, Agent, or Firm* — Timothy M. Brown, Esq.

(57) ABSTRACT

The disclosure relates to a method for correcting a fingernail or toenail, comprising the application of at least one layer and the performance of at least one treatment step, wherein the at least one layer contracts or expands, as well as a fingernail or toenail that can be produced with the method.

20 Claims, 2 Drawing Sheets

CORRECTIVE METHOD FOR FINGERNAILS OR TOENAILS

This application is a national phase patent utility filing under 35 USC §371, for International (PCT) Patent Application serial no. PCT/EP2010/064439, filed Sep. 29, 2010, which claims benefit of priority to German Patent Application Serial No. 10 2009 043 355.4 filed Sep. 29, 2009. The aforementioned applications are expressly incorporated by reference herein in their entirety for all purposes.

The disclosure relates to a method for correcting a fingernail or toenail, comprising the application of at least one layer and the performance of at least one treatment step, wherein the at least one layer contracts or expands, as well as a fingernail or toenail that can be produced with the method.

Corrective nail clamps are traditionally used for correcting ingrown or involuted fingernails and toenails. Plaster models of the nail to be corrected are prepared for this purpose, and spring-loaded clamps are produced precisely according to these models, comprising hook-like ends that grip around the edge of the nail and serve as a means of attachment for the clamp. This type of nail correction is indeed normally effective, but it has the disadvantage that the production of the plaster model and correspondingly dimensioned clamps is laborious. In addition, the hook-like ends of the clamp often do not obtain a secure hold onto such nails, so that they may break away laterally, leading to the growth of so-called "wild tissue".

To avoid the production of customized clamps for nail correction, the fastening of plates with open gaps onto the nail it is also known, and to engage into these gaps the ends of two clamp ends that encompass the nail, each with a lateral hook.

Thus in the patent application DE 10 2007 035 031 A1, an apparatus for correcting the growth of human nails is revealed that comprises an adhesive element, which is affixed with glue to a portion of the nail plate of a human toe. Here a force is exercised by a tension element that is firmly embedded in sections in the adhesive element, which imparts a bending moment upon the nail plate by an exertion of force outside the center, and lifts the nail edges.

The patent application DE 33 30 813 A1 discloses an apparatus to prepare for nail correction, comprising a means to fasten with the spring arrangement bound to the nail to be corrected.

The patent application DE 42 07 797 A1 discloses a corrective nail clamp, composed of two or more clasp components made of wire, which lie laterally over a portion of the nail and which are provided at one end with a hook that grips under the nail.

The patent application DE 32 36 804 A1 discloses a corrective nail clamp made of a spring steel band in a length required by the respective width of a toenail, for which a rubber form is slipped onto each end.

However, the disadvantage of these processes of prior art is that even with these attachment means generally clamps or similar means are used, which can lead to painful pressure points in the vicinity of the fingernail or toenail. Moreover, for extended periods of wear the hooks can also lead to serious inflammation, which if not treated may lead to the complete loss of the nail.

This disclosure therefore has the fundamental purpose of providing a method that does not exhibit the above-mentioned disadvantages of prior art. The method should be universally applicable and be able to be used without any discomfort for the user and independent of the form of the lateral edge of the nail and the nail bed (quick) in this region.

According to the disclosure, the problem has been solved by the method according to the accompanying claims, with which corrected fingernail and toenails may be produced.

For example, the method can be a cosmetic method, if for example the nail exhibits an undesirably high convex curvature that should be corrected. The method according to the disclosure is quick and simple to use, so that it is well suited to the high efficiency requirements in cosmetic practice. In comparison to the processes of prior art, the method according to the disclosure is generally painless, since metallic correctional aids can be avoided. The application of the layer occurs without intervention into the body, so that operative impacts are largely eliminated.

The fingernail or toenails produce an appealing esthetic effect due to the planar form created by the method according to the disclosure.

The method according to the disclosure makes it possible to dispense with a hook attachment on the edge of the nail entirely, and moreover it may be used for completely different nails to be treated.

In addition, the method can also be a therapeutic method, if a pathological change in the nail should be treated, such as for example a pathologically ingrown nail. In this case, the method is suited to the high efficiency requirements for medical and podiatric practice. By application of the method, nail bed infections can effectively be prevented.

Additional special implementations and advantageous effects are described in this application.

DETAILED DESCRIPTION OF THE DISCLOSURE

In a first aspect, the disclosure relates to a method for correcting a fingernail or toenail (2). The method comprises the following steps. In a first step a) at least one layer (3,4) of at least one compound will be applied to a fingernail or toenail. In a second step b) at least one treatment step will be performed, in which at least one of the applied layers (3,4) contracts or expands. Herein the degree of curvature of the fingernail or toenail (2) will be changed and the fingernail or toenail will be corrected.

In the sense of the disclosure, a "fingernail" or "toenail" is to be understood as any nail of a human or animal hand or of a human or animal foot. The fingernail or toenail is preferably a human fingernail or toenail. The disclosure relates in particular to a method for cosmetic correction of human toenails. In this case, the nail preferably has an undesirably high convex curvature, which should be corrected. Alternately the disclosure may also concern a therapeutic method, if a pathological change in the nail should be treated, such as for example a pathological ingrown nail, which has already led to frequent inflammation of the nail tissue or of the nail bed in the patient. In the sense of this application, under "correction" any method step shall be understood that can correct the undesirable curvature of the fingernail or toenail. For example, the reduction of the convexity of an ingrown nail shall be understood under correction, so that after correction the nail is primarily planar or at least exhibits minimal convexity.

In the first step a) at least one layer (3,4) of at least one compound will be applied to the fingernail or toenail. In other words, this means that the nail plate will be completely or at least partially covered with the layer composed of at least one compound. The application itself can occur through existing mechanical application processes, for example by dipping the fingernail or toenail in a liquid compound, by layered brushing of the compound, or by spray painting. Preferably the at least one layer will be applied with a brush onto the complete nail plate. The application may also preferably occur in multiple steps or levels, to achieve an extremely uniform, meaning planar distribution of the compound on the nail plate. Before the application, the nail can be softened or thinned, as well as clipped if necessary. It is particularly preferred that the nail plate should be mechanically roughened before application, since this leads to a very firm bond between the at least one layer and the nail plate.

The layer comprises at least one compound, which is preferably a polymer or a polymer composition, meaning a composition that comprises at least one type of polymer. The composition may generally be any compound(s) selected, so long as they are suitable for application to a fingernail or toenail, and the curvature of a fingernail or toenail can be corrected with their assistance. The composition is preferably a polymerized or polymerizable organic compound completely or partially dissolved in an aqueous or organic solvent. It is particularly preferred if the composition contains a co-polymerizable or graft-polymerizable oligomere or polymer compound. The compound may preferably contain at least one photo-polymerizable compound based upon acrylic acid esters. Any polymer may be used as the polymer, so long as they permit being hardened on the nail bed.

The compound may for example be a thermally hardenable adhesive compound that contains an organic resin and a cross-linking agent based upon Michael adducts of CH (hydrocarbon) acid, enolizable carboxylic acid esters with unsaturated alpha-beta-ethylene molecular groups. Alternatively the compound may also be a two-part enamel, which is thermally hardenable and simultaneously expandable or contractable, wherein the hardening reaction is catalyzed by a Lewis and/or Brönstedt base.

The compound may contain ester acrylates or ester methacrylates or a mixture thereof. Ester acrylates or ester methacrylates may be obtained for example by converting of acrylic acid or methacrylic acid with compounds having at least one OH-group or at least one epoxy group under condensation or addition. A variety of mono or multi-functional alcohols are generally suitable as the compound with at least one OH-group, preferably alcohols with two or more (for example 2 to 6), and in particular 2 or 3 OH-groups. Suitable alcohols may be both of aliphatic and also aromatic nature, or may contain both groups. Mono and multi-functional (meth) acrylate monomers are generally suitable, whereby this term (meth)acrylate stands both for compounds based on acrylic acid and also for compounds based on methacrylic acid. Typical examples of this class of compounds (described for example in DE-A-43 28 960) are alkyl (meth)acrylates, including the cyclo-alkyl(meth)acrylates, aralkyl(meth)acrylates, and 2-hydroxyalkyl(meth)acrylates, for example hydroxypropyl methacrylate, hydroxyethyl methacrylate, isobornyl acrylate, isobornyl methacrylate, butylglycol methacrylate, acetyl glycol methacrylate, triethylene-glycol dimethacrylate, polyethylene glycol dimethacrylate, 2-phenylethyl methacrylate, 2-ethylhexyl methacrylate, cyclohexyl methacrylate, lauryl methacrylate and hexane-diol-di(meth)acrylate. Long-chain monomers based on bis-phenol A and glycidyl methacrylate may also be used, which are known from U.S. Pat. No. 3,066,112, or their derivatives resulting from addition of isocyanates (urethane methacrylate). Compounds of the type bis-phenol-A-diethyloxy(meth)acrylate and bis-phenol-A-dipropyloxy(meth)acrylate are also suitable. In addition, the oligoethoxylated and oligopropoxylated bis-phenol-A-diacryl- and -dimethyl acryl-acid ester may find use. Well suited are also the diacryl- and dimethyl-acrylic acid ester of bis(hydroxymethyl)-tricyclo[5.2.1.026]-decane mentioned in DE-C-28 16 823 and the diacryl- and dimethacrylic acid ester extended with 1 to 3 ethylene oxide and/or propylene oxide groups compound of bis(hydroxymethyl)-tricyclo[5.2.1.026]-decane. The production of appropriate ester acrylates or ester methacrylate is general known by experts.

The compound may also contain urethane methacrylate or multi-functional urethane acrylates. Urethane methacrylates can be obtained by conversion of polyisocyanate with OH-functional acrylates or methacrylate such as hydroxyethyl-acrylate, hydroxypropyl acrylate hydroxyethyl-methacrylate or hydroxypropyl methacrylate. If a di-isocyanate is used as polyisocyanate, then a urethane dimethacrylate is obtained as product, by using an OH-functional acrylate, one similarly obtains a bi-functional acrylate. Urethane methacrylate or urethane acrylates exhibit excellent characteristics, such as high stiffness. The use of a combination of tri-isocyanates or superior grade polyisocyanates produced from OH-functional acrylates or methacrylate monomers is also possible, whereby such types of urethane methacrylates or urethane acrylates exhibit a functionality of three or more with regard to olefinic unsaturated double bonds.

An appropriate compound suitable for production as polymerizer may contain yet one or more reaction solvent(s) in addition to the above mentioned components. Within the scope of the present application, the term reaction solvent is understood to encompass all compounds, that affect the compound used as polycondensate as solvent or diluter, and thereby reduce the viscosity of the compound, which however are in addition polymerized into the polymer matrix during the polymerization of compound, for example by polymerization with assistance of light or heat. Also suitable are for example additional monomethacrylates, dimethacrylates, and trimethacrylates. Thus for example, dimethacrylate co-monomers such as tri-ethylene glycol dimethacrylate ("TEGDM"), ethylene glycol dimethacrylate, tetramethylene glycol dimethacrylate, trimethylol-propyl tri-methacrylate, 1,6-Hexan-diol dimethacrylate, and 1,3-butanediol dimethacrylate are suitable as additional components of the compound to be polymerized.

In addition, a polymeric compound used for polymerization may contain additional materials such as fillers, photo-initiator systems and coloration pigments.

The compound may also contain A) 10% to 90% by weight of one or more compound acting as cross-linker with an average of at least two CH-acidic hydrogen atoms, which come from one or more of the following groups and may be the same or different: within —CN or —NO2 or —CN, —H, alkyl or alkylene, whereby the remainder are bound respectively to the carbon atom in the CH-group and the CH-group is bound to at least one of the remainder to a polymer or oligomer unit, B) 90% to 10% by weight of one or more (meth)acryl copolymerizers suitable for Michael addition, polyester and/or polyurethane resins with at least two alpha-beta-unsaturated groups bound via the carbonyl-carbon atom, and C) 0.01% to 5% by weight with respect to the sum of the weights of the components A) and B) of a catalyst in the form of a Lewis or Brönstedt base compound, wherein the conjugated acids of the latter have a pKA-value of at least 10.

The compound may also contain a polyurethane or a polyurethane mixture. The polyurethane is preferably selected from hydrophilic, water-soluble or water-dispersing polyurethanes with ionogenic or ionic groups. As polyurethane may for example be used: a polyurethane that is formed from a polyol-component, which may be an alkylene glycol, a polyoxy-alkylene glycol or a linear polyester diol, a carboxylic acid ester component with hydroxyl or amino groups, and an organic isocyanate or isocyanate precursor, whereby the ester groups bound to the polymer backbone after polymerization are saponified; a polyurethane formed from a) at least one compound that contains two or more active hydrogen (atoms) per molecule, b) diol comprising at least one acid or salt groups, and c) at least one di-isocyanate; a polyurethane, formed from a) at least one di-isocyanate, which may already be combined with one or more compound(s) that contain(s) two or more active hydrogen atoms per molecule, and b) at least one diol, a primary or secondary amino-alcohol, a primary or secondary di-amine or a primary or secondary tri-amine with one or more tertiary, quarternary or protonated tertiary amine-nitrogen atoms; a polyurethane with carboxylate groups and an amount of monomer dials of the form A-C(CH$_2$OH)$_2$—COOH wherein A stands for a hydrogen atom or a C$_1$- to C$_{20}$-alkyl group; a polyurethane formed from a) a water-soluble or dispersing polyurethane pre-polymer with terminal isocyanate groups, and b) at least one primary or secondary amine that comprises at least one ionogenic or ionic group. For example, hexamethylene di-isocyanate, 2,4- and 2,6-toluene di-isocyanat, 4,4'-methylene di(phenylisocyanat), or isophoron di-isocyanate may be used as di-isocyanate. Alternatively, the polymer may also be from a natural source. As glycol component, a compound may be chosen that is selected from ethylene glycol, the propylene and butylene glycols, di-, tri-, tetra-, and polyethylene and polypropylene glycols, copolymers of alkylene oxides such as ethylene oxide, propylene oxide, or butylene oxide, ethylene di-amine, propylene di-amine, 1,4-diaminobutane, hexamethylene di-amine, and alpha-, omega-di-amines from long-chain alkanes or polyalkylene oxides. The compound may in addition also contain one or more natural polymer(s). For example, the compound may also contain a natural polymer that is selected from shellac, chitosan, alkoxylated chitosans, alkoxylated chitines, polysaccharides, and Chinese balsam resin.

The compound may contain one or more photo initiators, which by irradiation with UV or visible light may trigger the polymerization reaction. The polymeric compound intended for polymerization may for example contain as photo initiators individual suitable photo initiators. It is however also possible that the polymeric compound used for polymerization also contains initiating systems that comprise photo initiators and co-initiators. Representatives of such photo initiators are for example benzoic alkyl ether, benzil ketals, acylphosphine oxide, or aliphatic and aromatic 1,2-diketone compounds, for example camphor quinone, whereby the light polymerization can be accelerated in a manner that is known by the addition of activators, such as tertiary amines or organic phosphites. Suitable initiating systems for triggering the polymerization via a redox mechanism are for example systems of peroxide/amine or peroxide/barbituric acid derivatives. For the use of such initiating systems, it is expedient to keep an initiator (such as peroxide) and a catalyst component (such as amine) separately available. The two components are then briefly mixed uniformly with each other before application.

The compound may be dissolved in one or more organic solvent(s), which are preferably mixable with water. For example, ethanol, propanol, isopropanol, acetone, methylethyl ketone, acetic acid methylester, or acetic acid ethyl ester, or a mixture of two or more of these may be used as solvent.

The at least one compound is preferably primarily liquid, meaning a thin fluid, viscous, or viscid, or generally gelatinous. In this manner, the compound may be better applied onto the nail. The compound should be hardenable after application, meaning strengthenable, in order to produce a primarily firm layer. In an implementation, the hardening of the layer will thereby be attained after application, in that the solvent evaporates, leaving a hardened layer behind. The evaporation of the solvent can be performed at room temperature, or the layer may be additionally heated, for example by use of a hot air blower, in particular at temperatures in the range of 40° C. to 60° C. In another implementation, the layer can thereby be hardened, in that the monomers, oligomers, or polymers contained in the compound cross-link or polymerize. In this case, the cross-linked polymer compound ensures for the firmness of the resulting layer.

In the second step b), at least one treatment step will be performed, wherein the at least one layer (3,4) either contracts, meaning shortens, or expands, meaning lengthens. Hereby the degree of curvature, meaning the convexity level of the fingernail or toenail (2), will be changed and the fingernail or toenail thus corrected. In an especially preferred implementation, the layer contracts during hardening. Due to the tension stress during contraction and hardening of the compound onto the nail plate, this will be lifted at its edges, so that the fingernail or toenail exhibits minimal curvature after step b) and thus is corrected.

The thickness of the applied layer can be freely selected, so long as it is suitable to correct the fingernail or toenail. The thickness of the applied layer is preferably 100 µm to 1 mm, especially preferable 200 µm to 800 µm, in particular 300 µm to 500 µm.

In a preferred implementation, the at least one treatment step in step b) is a light or thermal treatment step.

For example, the at least one layer (3,4) may contract due to a thermal treatment step because of chemical or physical changes within the intrinsic structure of the layer. For example, the fingernail or toenail may exhibit a thermal expansion coefficient different from that of the at least one layer, so that the fingernail or toenail bends in opposition to the curvature of the fingernail or toenail due to the thermal expansion or the thermal contraction, in the direction of reduced convexity. If the compound applied in step a) contains a polymerizable oligomer or polymer, the thermal treatment may also initiate (meaning start) a second polymerization reaction, which leads to a polymer compound or copolymerized compound with a reduced spatial volume, so that tension stress in direction of the center of the fingernail or toenail will be caused because of the polymerization method.

In an alternative implementation, the treatment step is a photo treatment step, meaning a treatment by irradiation of light of a certain wavelength. For example, light treatment may occur with ultraviolet (UV) light with a wavelength of less than 400 nm, or less than 315 nm, or less than 280 nm. The use of blue light in the range of 435 nm to 495 nm is particularly preferred, since this is less risky in view of cancer-causing effects in longer or more intense irradiation, and is thus to be preferred for medical reasons. By irradiation with light of a certain wavelength, the spatial or chemical structure within the layer changes in such a manner that the layer itself contracts or expands, preferably contracts. If the polymerizable compound applied in step a) contains oligomers or polymers, then the irradiation with UV-light may creates for example radicals, which can be initiators of a radical polymerization or copolymerization. If the layer contracts during such a polymerization or copolymerization, correction of a nail may be achieved.

Alternatively, a phase change in the at least one layer may also be evoked by the light or thermal treatment, which is accompanied by an expansion or contraction of the at least one layer. If for example the at least one applied layer (3,4) is an amorphous thermoplastic, then a phase change can occur by heating above the glass transition temperature $T_G$, whereby the layer converts to a phase with reduced or increased spatial volume. Here the nail will be bent in the direction of reduced convexity and thereby corrected.

In an additional implementation, the at least one treatment step is a cold treatment step. By cold treatment, a plastic, for example an elastomer, can pass below the glass transition temperature into a crystalline phase, which occupies a lesser or a higher spatial volume. Hereby the correction of the fingernail or toenail will be achieved.

In yet another additional alternative implementation, the treatment step is a swelling or shrinking step. In this case the at least one applied layer (3,4) will be exposed to an aqueous or organic solvent. Through diffusion of solvent out of the at least one layer, or diffusion of solvent into the at least one layer a swelling or shrinking of the layer will be caused, which expands or contracts the layer. In other words, through the selection of a chemically defined polymer as component of the compound and a corresponding solvent, a selective enrichment or reduction of the solvent in the layer will be achieved, which contracts or expands the layer.

The at least one treatment step can also occur thereby, in that the at least one layer will be exposed to an electric voltage, which causes a phase change within the layer. For example, the crystallization level may be change, by the treatment step, so that the layer contracts or expands.

Additional treatment steps, which can change the spatial volume of an applied layer, are known to experts.

The at least one layer (3,4) is preferably hardened during the execution of the at least one treatment step in step b). Harden in the sense of this application means that the layer becomes firm. For example, the layer may exhibit a higher modulus of elasticity after hardening.

If the at least one layer is hardened during the execution of the at least one treatment step in step b), then an intermediate step of hardening after the application of the layer and step b) is unnecessary. In this case, the bending of the nail will be achieved by simultaneous hardening and firming of the at least one layer, so that this method is particularly efficient.

In an alternative implementation, the at least one layer (3,4) hardens after the application in step a) and before the execution of the at least one treatment step in step b). If the at least one layer hardens after the application in step a) and before the execution of the at least one treatment step in step b), then the stiffening, meaning the hardening of the layer, and the expansion or contraction of layer can be performed separately from one another under optimum conditions, without necessitating compromise solutions with regard to optimum hardening and the desired expansion or contraction.

In a preferred implementation, the modulus of elasticity of the at least one layer (3,4) lies in the range of 1 to 50 kN/mm² after the treatment step in step b), preferably in the range of 10 to 30 kN/mm², in particular in the range of 15 to 25 kN/mm².

The hardened layer preferably exhibits a modulus of elasticity that lies above the modulus of elasticity of the fingernail or toenail. In this manner, the forces released can be efficiently transferred to the fingernail or toenail by the contraction or expansion of the layer, so that it can be corrected very effectively. On the other hand, the modulus of elasticity of the hardened layer should not be so high that the layer causes unpleasant pressure points or even inflammation on the nail for longer use. For this reason, it is preferable that the modulus of elasticity lies below the modulus of elasticity of steel, thus below approximately 200 kN/mm².

In a preferred implementation, at least one first layer (3) will be applied in step a) onto the fingernail or toenail (2). Subsequently the at least one second layer (4) will be applied onto the at least one first layer. The at least one first layer (3) and the at least one second layer (4) are differentiated with regard to their chemical composition.

The at least one first layer (3) and the at least one second layer (4) may exhibit the characteristics described above for the at least one layer (3,4).

Initially a first layer composed of a compound is preferably applied and hardened onto the fingernail or toenail. Then a second layer composed of a second compound different from the compound of the first layer will also be applied and hardened onto the first layer. If necessary additional layers may be applied in this manner, wherein an entire laminated structure with a multiplicity of layers forms the coating of the nail. Preferably the at least one second layer is generally firmly connected with the at least one first layer, so that a good force transmission exists between the layers, if one or more of these layers expands or contracts. For example, the first layer may be a polymer layer, which can harden by evaporation of solvent, and the second layer can also be a polymer layer, which can harden by evaporation of solvent. In this case the treatment step may be a photo treatment step, in which only the second layer cross-links further in the treatment step b) and thus contracts in relationship to the first layer. The treatment step may also be designed that a cross-linking catalyst will be applied to the second layer. This can catalytically initiate the cross-linking reaction. The treatment step may furthermore be an ultrasonic treatment step. In this case, the cross-linking reaction may for example be initiated by impingement by ultrasonic waves. The cross-linking in the second layer can cause a correction of the nail opposite to the undesirable curvature due to the planar tension force $F_X$ (see FIG. 2) occurring in the direction of the center of the nail because of the volume reduction during the reaction.

The use of at least two layers with different chemical compositions has the advantage that the layers can bend more strongly overall and the nail can still be corrected effectively in this manner. The more layers that are used, the more effective the nail correction is. On the other hand, the application of more than 5 or more than 10 layers will tend to be very time-consuming, which frequently leads to a limited acceptance of the treatment method by users. For this reason it is preferable not to apply more than 5 or 10 layers.

If more than one layer (3,4) will be applied, then each of the layers (thus for example both the first layer (3) and also the second layer (4)) preferably comprises a thickness of 100 μm to 1 mm, particularly preferably 200 μm to 800 μm, in particular 300 μm to 500 μm. The overall thickness of all layers lies preferably in the range of 500 μm to 2 mm.

In a preferred implementation, the at least one first layer (3) contracts during the treatment step in step b).

In other words, only the most exterior layer of the multiple layers on to the fingernail or toenail contracts over the area of application, for example the second of two layers, whereas the inner layer, for example the first of two layers, either does not contract or even expands, which is preferred.

In a preferred implementation, the at least one second layer (4) expands during the treatment step in step b).

In other words, the innermost layer, or the innermost layers in the case of multiple layers on the fingernail or toenail expands itself in the area of application, for example the first of two layers, whereas the most exterior layer or the most exterior layers, for example the second of two layers, either does not expands or even contracts.

In a preferred implementation, the at least one first layer (3) contains poly(4-vinyl pyridine). The at least one second layer (4) contains polystyrene.

A solution of poly(4-vinyl pyridine) (P4VP) in chloroform or toluene is preferably applied to the nail as first layer (3). Here the application method is just as described above. After evaporation of the solvent, a solution of polystyrene (PS) in chloroform or toluene will be applied onto the first layer. This second layer will then also be hardened by evaporation of the solvent. The treatment step subsequently comprises contacting the layer with an aqueous solution. The aqueous solution is preferably a solution of dodecylbenzene sulfonic acid (DBSA) in water, particularly preferably 0.1 to 100% by weight of DBSA in water, particularly preferably 0.5% to 10% by weight of DBSA in water, for example 2% by weight of DBSA in water. The fingernail or toenail is preferably completely immersed in the aqueous solution over a long time period, preferably at least multiple minutes, up to multiple hours in especially serious cases.

Without being bound to one theory, it shall be assumed that a supra-molecular complex with the pyridine ring of the P4VP is formed by the treatment step, which leads to a higher specific volume of the polymer in the first layer. Since the layer of polystyrene normally neither generally expands nor contracts in contact with the aqueous solution, resulting in a bending moment, which leads to a lifting of the nail at its edges, so that the nail will be corrected with regards to stronger convexity.

In a preferred implementation, a protective layer will be applied additionally onto the at least one layer (3,4) in step a).

Initially a first layer composed of a compound is preferably applied to the nail and hardened. Then a second layer composed of another compound will be applied to the nail and hardened. The protective third layer will be applied onto the second layer. The protective layer may be any layer that can protect the underlying layer or the underlying layers in regard to mechanical or chemical stability. The protective layer is preferably also composed of a polymer or a polymer composition, in particular of cross-linked polymers or copolymers. The application method is just as described above.

It has proved to be advantageous to protect the at least one layer (3,4) from mechanical or chemical effects by use of a protective layer. In this manner, the layer can be left on the nail by the user for a longer time period, in particular for a time period of several months, for example at least three months, or at least six months, whereby the corrective effect of the layers on nail growth lasts for a long time. In this manner, the layers do not need to be newly applied regularly, but instead one session is normally enough to correct the fingernail or toenail over a time period of 6 months to 2 years.

In a preferred implementation, the steps a) and b) are repeated multiple times.

For example, the steps a) and b) can be repeated in this order at least twice, or at least three times, or at least five times. If the steps a) and b) are repeated multiple times, then a more uniform correction of the fingernail or toenail is produced and the strength of the curvature may be set individually. Ordinarily the correction of the nail occurs more strongly when the steps a) and b) are repeated more often.

In a preferred implementation, the method additionally comprises a step c) to chemically and/or mechanically remove the layer (3,4) from the fingernail or toenail (2).

The at least one layer (3,4) may be removed from the nail in any existing chemical and/or mechanical manner. For example, the layer can be stripped away from the nail with a file, with emery or sandpaper, or with a mill. Alternatively, an organic solvent can also be used to dissolve the layer away from the nail. In a preferred implementation, chemical and mechanical method steps are alternated, for example filing and dissolving with organic solvent.

After removal of the at least one layer (3,4) the correction of curvature of the fingernail or toenail preferably is retained. Removal of the layer is preferably performed so that after removal of the layer, the nail re-attains its natural appearance again, in particular with regard to shine and its surface characteristics.

In a preferred implementation, the at least one layer (3,4) remains permanently on the nail, grows out with the nail, and is cut off of the front (edge) together with the nail.

The at least one layer (3,4) is preferably generally colorless or exhibits a color corresponding to one of the natural shades of the nail plate or of the nail bed.

In this manner, the natural shading of the fingernail or toenail will be imitated during the wearing of the at least one layer, and this results a very esthetic overall appearance. The use of generally colorless layers is also otherwise preferred, in that irregularities may be quickly recognized, for example, separation of the layer or intolerance of the nail for the applied layer.

To achieve a natural shading, the layer may also contain pigments, such as for example titanium oxide, as well as any coloration pigment materials permitted for use in decorative cosmetics, as well as pigments produced with metal oxide coated reflective plates that are reflective when viewed. The layer may also contain other solid material, so long as their presence does not disturb the contraction or expansion of the layer. For example, the layer may contain highly dispersed free silica for adjusting the viscosity.

In an additional aspect, the present disclosure is related to a fingernail or toenail (2) that is produced by the method according to the disclosure.

The present disclosure will now be further explained based on individual examples and figures. These examples and figures serve only to depict the general inventive design; the examples and figures shall not comprise a limiting character on the protective scope.

SHORT DESCRIPTION OF THE FIGURES

EXAMPLES

Figure 1:
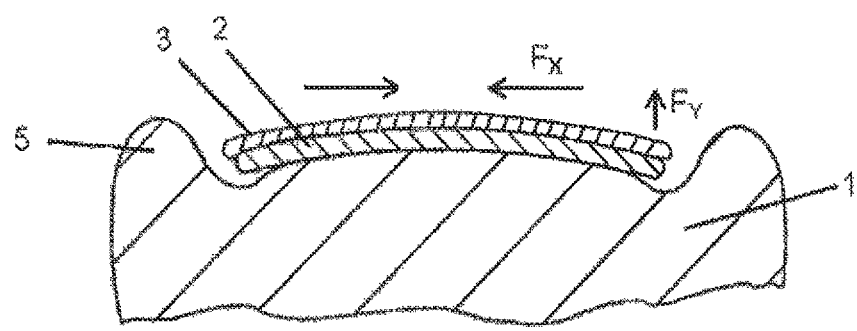
FIG. 1 shows a method for correcting a human fingernail or toenail (2) by using a contracting layer (3).

Corresponding to FIG. 1, a method for nail correction on a human foot or a human hand (1) with use of a layer (3) is shown, wherein the layer can contract. The layer is composed of a compound, which contains single or multiply functional or functionalized urethane acrylates, partially acrylated epoxy resins, such as for example bis-phenol-A-epoxy acrylate, single or multiply functional or functionalized acrylate oligomers as cross-linker, single or multiply functional or functionalized acrylate monomers as reactive diluter, and common UV initiators, such as for example 2-hydroxy-2-methyl-1-methylpropane-1-on (HMPP) with 2,4,6-trimethyl benzoyl diphenyl phosphine oxide. The layer is thinly applied to the nail plate (2) with a brush in liquid phase, so that the layer completely covers the upper surface, meaning laterally to the nail fold (5) and lengthwise from the cuticle to the free-lying edge of the nail (hyponychium). The thickness of the layer is approximately 200 μm to 300 μm. The compound is then hardened, in that the applied layer is radiated by a UV lamp (60 Watt, wavelength 380 nm to 450 nm) for a time period of 1 minute, whereby the layer hardens. The applied layer simultaneously contracts, so that forces $F_X$ in direction of the center of the nail plate act. The nail plate itself remains generally constant with regard to its dimensions under the conditions of the treatment step, meaning it does not contracts or expand. Hereby a vertical force $F_Y$ acts on the edge of the nail plate opposite to the rolling or curvature, so that a correction of the nail will be achieved.

Figure 2:
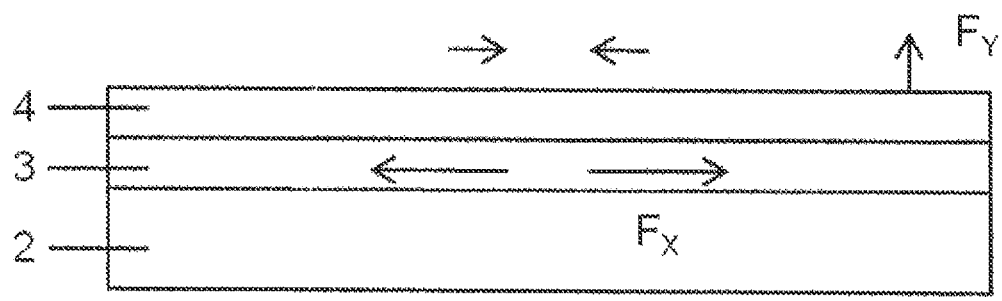
FIG. 2 shows a method for correcting a human fingernail or toenail (2) by using two layers (3,4).

Corresponding to FIG. 2, a method for correcting a human fingernail or toenail (2) by using two layers (3,4) is shown. The inner layer (5) is a layer of poly(4-vinyl pyridine) (P4VP) that can expand, and the outer layer (3) is a layer of polystyrene (PS), which generally does not change. The poly(4-vinyl pyridine)-layer and the polystyrene-layer are applied onto the fingernail or toenail in a solution of chloroform or toluene by dipping, dabbing, or painting. The thickness of the layer (measured by ellipsometry) amounts to approximately 200 μm, both for the poly(4-vinyl pyridine)-layer as well as the polystyrene-layer. The layers were hardened by irradiation with short wave UV light (lambda=254 nm, radiation dose W=4 J cm-2) with use of a photo-mask to protect the skin components. UV-light in the short wave spectrum leads to a cross-linking of both polymers (see S. Timoshenko, J. Opt. Soc. Am. 1925, 11, 233). After hardening of the layer, the fingernail or toenail is immersed in an aqueous solution of 2% by weight of dodecylbenzene sulfonic acid (DBSA), whereby a supra-molecular complex forms with the pyridine ring of P4VP. Here the specific volume of the polymer in the inner layer will be increased. Since the polystyrene-layer is not affected in this solution, meaning in particular that it does not exhibit the same expansion as the P4VP-layer, a bending opposite to the undesirable curvature of the nail is obtained.

The invention claimed is:

1. A method for correcting a fingernail or toenail (2), comprising at least the following steps:
   a) coating a fingernail or toenail with at least one layer (3,4) of at least one compound, and
   b) performing of at least one treatment step, in which the at least one layer contracts or expands, wherein the degree of curvature of the fingernail or toenail (2) changes and the fingernail or toenail will thus be corrected.

2. The method according to claim 1, whereby the at least one treatment step in step b) is a light or thermal treatment step.

3. The method according to claim 2, whereby the at least one layer (3,4) is hardened during the performance of the at least one treatment step in step b).

4. The method according to claim 3, whereby the modulus of elasticity of the at least one layer (3,4) lies in the range from 1 to 50 kN/mm$^2$ after the performance of the at least one treatment step in step b).

5. The method according to claim 2, whereby the at least one layer (3,4) is hardened after the application in step a) and before the performance of the at least one treatment step in step b).

6. The method according to claim 5, whereby the modulus of elasticity of the at least one layer (3,4) lies in the range from 1 to 50 kN/mm$^2$ after the performance of the at least one treatment step in step b).

7. The method according to claim 2, whereby the modulus of elasticity of the at least one layer (3,4) lies in the range from 1 to 50 kN/mm$^2$ after the performance of the at least one treatment step in step b).

8. The method according to claim 2, whereby in step a) at least one first layer (3) is applied onto the fingernail or toenail (2), and at least one second layer (4) is applied onto the at least one first layer (3), wherein the at least one first layer (3) and the at least one second layer (4) are different with regard to their chemical composition.

9. The method according to claim 8, whereby the modulus of elasticity of the at least one layer (3,4) lies in the range from 1 to 50 kN/mm$^2$ after the performance of the at least one treatment step in step b).

10. The method according to claim 9, whereby the at least one first layer (3) expands during the treatment step in step b).

11. The method according to claim 9, whereby the at east one second layer (4) contracts during the treatment step in step b).

12. The method according to claim 1, whereby the at least one layer (3,4) is hardened during the performance of the at least one treatment step in step b).

13. The method according to claim 1, whereby the at least one layer (3,4) is hardened after the application in step a) and before the performance of the at least one treatment step in step b.

14. The method according to claim 1, whereby the modulus of elasticity of the at least one layer (3,4) lies in the range from 1 to 50 kN/mm$^2$ after the performance of the at least one treatment step in step b).

15. The method according to claim 1, whereby in step a) at least one first layer (3) is applied onto the fingernail or toenail (2), and at least one second layer (4) is applied onto the at least one first layer (3), wherein the at least one first layer (3) and the at least one second layer (4) are different with regard to their chemical composition.

16. The method according to claim 15, whereby the at least one first layer (3) expands during the treatment step in step b).

17. The method according to claim 15, whereby the at least one second layer (4) contracts during the treatment step in step b).

18. The method according to claim 1, whereby in step a), after the application of the at least one layer (3,4), a protective layer is additionally applied onto the at least one layer (3,4).

19. The method according to claim 1, comprising the following step in addition:
   c) chemically or mechanically removing of the layer from the fingernail or toenail (2).

20. The method according to claim 1, wherein the at least one layer (3,4) is substantially colorless or exhibits a color corresponding to the natural shade of the nail plate or of the nail bed.

* * * * *